United States Patent
Bolognini et al.

(10) Patent No.: US 9,744,116 B2
(45) Date of Patent: Aug. 29, 2017

(54) HIGH COLOR INTENSITY AND EASILY REMOVABLE MASCARA

(71) Applicant: L'OREAL, Paris (FR)

(72) Inventors: Marie K. Bolognini, Somerset, NJ (US); Kavita Patel, East Windsor, NJ (US); Angeles Fonolla-Moreno, Westfield, NJ (US)

(73) Assignee: L'OREAL, Paris (FR)

( * ) Notice: Subject to any disclaimer, the term of this patent is extended or adjusted under 35 U.S.C. 154(b) by 216 days.

(21) Appl. No.: 14/030,288

(22) Filed: Sep. 18, 2013

(65) Prior Publication Data

US 2015/0079016 A1    Mar. 19, 2015

(51) Int. Cl.
| | |
|---|---|
| *A61K 8/00* | (2006.01) |
| *A61K 8/81* | (2006.01) |
| *A61Q 1/00* | (2006.01) |
| *A61Q 1/10* | (2006.01) |
| *A61K 8/86* | (2006.01) |
| *A61K 8/34* | (2006.01) |
| *A61K 8/19* | (2006.01) |
| *A61K 8/84* | (2006.01) |
| *A61K 8/895* | (2006.01) |
| *A61K 8/362* | (2006.01) |
| *A61K 8/891* | (2006.01) |
| *A61K 8/60* | (2006.01) |
| *A61K 8/92* | (2006.01) |
| *A61K 8/02* | (2006.01) |
| *A61K 8/06* | (2006.01) |
| *A61K 8/37* | (2006.01) |
| *A61K 8/894* | (2006.01) |

(52) U.S. Cl.
CPC ............ *A61K 8/8152* (2013.01); *A61K 8/027* (2013.01); *A61K 8/062* (2013.01); *A61K 8/19* (2013.01); *A61K 8/34* (2013.01); *A61K 8/345* (2013.01); *A61K 8/362* (2013.01); *A61K 8/375* (2013.01); *A61K 8/60* (2013.01); *A61K 8/604* (2013.01); *A61K 8/8111* (2013.01); *A61K 8/84* (2013.01); *A61K 8/86* (2013.01); *A61K 8/891* (2013.01); *A61K 8/894* (2013.01); *A61K 8/895* (2013.01); *A61K 8/922* (2013.01); *A61K 8/927* (2013.01); *A61Q 1/00* (2013.01); *A61Q 1/10* (2013.01); *A61K 2800/30* (2013.01); *A61K 2800/43* (2013.01)

(58) Field of Classification Search
CPC ............ A61K 2800/30; A61K 2800/43; A61K 8/027; A61K 8/062; A61K 8/19; A61K 8/34; A61K 8/60; A61K 8/8111; A61K 8/8152; A61Q 1/00; A61Q 1/10
See application file for complete search history.

(56) References Cited

U.S. PATENT DOCUMENTS

| | | | |
|---|---|---|---|
| 5,866,111 A | 2/1999 | Felardos et al. | |
| 6,372,201 B1 | 4/2002 | Leuridan et al. | |
| 6,416,768 B1 | 7/2002 | Ravaux et al. | |
| 6,562,356 B2 | 5/2003 | Verite et al. | |
| 6,689,371 B1 | 2/2004 | Simonnet et al. | |
| 7,087,650 B2 | 8/2006 | Lennon | |
| 7,094,842 B2 | 8/2006 | Lennon | |
| 7,217,424 B2 | 5/2007 | Pereira et al. | |
| 7,611,725 B2 | 11/2009 | Pereira et al. | |
| 7,879,316 B2 | 2/2011 | Ferrari et al. | |
| 8,080,239 B2 | 12/2011 | Matsuo et al. | |
| 8,512,683 B2* | 8/2013 | SaNogueira | A61K 8/06 424/401 |
| 8,920,787 B2* | 12/2014 | Li | A61Q 1/10 424/70.11 |
| 2001/0028887 A1 | 10/2001 | Douin et al. | |
| 2002/0098215 A1 | 7/2002 | Douin et al. | |
| 2003/0171479 A1* | 9/2003 | Lennon | A61K 8/06 524/501 |
| 2005/0112072 A1 | 5/2005 | Wang et al. | |
| 2006/0078524 A1 | 4/2006 | Midha et al. | |
| 2006/0078527 A1 | 4/2006 | Midha et al. | |
| 2006/0193813 A1 | 8/2006 | Simonnet | |
| 2007/0065392 A1 | 3/2007 | Simonnet | |
| 2007/0077221 A1* | 4/2007 | Seigneurin | A61K 8/8152 424/70.16 |
| 2007/0292377 A1 | 12/2007 | Ide et al. | |

(Continued)

FOREIGN PATENT DOCUMENTS

| | | |
|---|---|---|
| EP | 0792636 A1 | 9/1997 |
| EP | 0898953 A2 | 3/1999 |

(Continued)

OTHER PUBLICATIONS

Marti-mestres et al. Optimization with Experimental Design of Nonionic, Anionic, and Amphoteric Surfactants in a Mixed System. Drug Development and Industrial Pharmacy, 23( lo), 993-998 (1997).*

(Continued)

*Primary Examiner* — Robert A Wax
*Assistant Examiner* — Olga V Tcherkasskaya
(74) *Attorney, Agent, or Firm* — Oblon, McClelland, Maier & Neustadt, L.L.P.

(57) ABSTRACT

Disclosed are low wax mascara compositons comprising a liquid fatty substance, an emulsifying system including a sucrose fatty acid ester and a co-emulsifier, a viscosity increasing agent, a film forming system including a film forming polymer and a co-film former, and water. Also disclosed are methods for making up and/or enhancing the appearance of eyelashes by applying said compositions to the lashes.

26 Claims, 7 Drawing Sheets

(56) References Cited

U.S. PATENT DOCUMENTS

| | | |
|---|---|---|
| 2008/0014164 A1 | 1/2008 | Jacquier |
| 2008/0095730 A1 | 4/2008 | Atis |
| 2008/0124291 A1 | 5/2008 | Arditty |
| 2008/0213198 A1 | 9/2008 | Lintner et al. |
| 2008/0279901 A1 | 11/2008 | Prigent et al. |
| 2009/0105353 A1 | 4/2009 | Lorant |
| 2010/0028284 A1* | 2/2010 | Atis ............ A61Q 1/10 424/70.7 |
| 2010/0190740 A1* | 7/2010 | L'Alloret .......... A61K 8/0295 514/53 |
| 2011/0274636 A1 | 11/2011 | Perruna et al. |
| 2011/0293550 A1 | 12/2011 | Bui et al. |
| 2012/0230927 A1 | 9/2012 | Gallagher et al. |
| 2013/0287724 A1* | 10/2013 | Hoffman ............ A61Q 17/00 424/78.05 |

FOREIGN PATENT DOCUMENTS

| | | |
|---|---|---|
| EP | 1604632 A1 | 12/2005 |
| EP | 1671620 A1 | 6/2006 |
| EP | 1787628 A1 | 5/2007 |
| EP | 1834633 A2 | 9/2007 |
| EP | 1857433 A1 | 11/2007 |
| FR | 2886847 A1 | 12/2006 |
| FR | 2917965 A1 | 1/2009 |
| FR | 2945208 A1 | 11/2010 |
| FR | 2957255 A1 | 9/2011 |
| JP | 2004075639 A | 3/2004 |
| KR | 20010017533 A | 3/2001 |
| WO | 2007054824 A2 | 5/2007 |
| WO | 2007074331 A1 | 7/2007 |
| WO | 2012078751 A2 | 6/2012 |
| WO | 2012174091 A2 | 12/2012 |
| WO | 2012174096 A2 | 12/2012 |
| WO | 2013049599 A2 | 4/2013 |

OTHER PUBLICATIONS

Bouchemal t al. Nano-emulsion formulation using spontaneous emulsification: solvent, oil and surfactant optimisation. International Journal of Pharmaceutics 280 (2004) 241-251.*

Anderson et al. Find the Optimal Formulation for Mixtures. Stat-Ease Inc., Minneapolis (2002), 8p.*

Patent Cooperation Treaty, International Search Report, Application PCT/EP2014/067713, mailed Dec. 11, 2014, European Patent Office, P.B. 5818 Patentlaan 2, NL-2280 HV Rijswijk.

U.S. Appl. No. 14/030,233, filed Sep. 18, 2013, Marie K. Bolognini.

U.S. Appl. No. 13/731,286, filed Dec. 31, 2012, Patel et al.

U.S. Appl. No. 13/848,822, filed Mar. 22, 2013, Alden-Danforth et al.

Response filed Oct. 30, 2014 to Restriction Requirement dated Oct. 21, 2014 in U.S. Appl. No. 14/030,233.

* cited by examiner

HIGH COLOR INTENSITY AND EASILY REMOVABLE MASCARA

FIELD OF THE INVENTION

The present invention generally relates to a novel mascara composition that is low wax or wax-free, contains a sucrose fatty acid ester and is easy to remove. The invention also relates to methods of making up eye lashes with improved removability.

BACKGROUND OF THE INVENTION

Several different mascara compositions have been developed in the art using various ingredients to impart desired cosmetic properties. For example, mascaras typically contain wax which is used to provide body and volume. However, the tackiness of the wax leads to mascara compositions that clump, apply unevenly, dry the lashes, smudge, flake and are difficult to remove. Also, the tackiness of the wax limits the buildability (layering) and playtime (smoothness) of these waxes. When the wax is eliminated from the mascaras to facilitate application and removal, the compositions also lose desirably properties and tend to be runny.

The current invention provides low wax and/or wax free mascara compositions having a creamier, silkier and more hydrating or "wet" texture as compared to traditional mascaras. These compositions provide a light and soft feel to the lashes while at the same time affording good body and volume to the lashes. The compositions of the invention can be applied to lashes easily and yield smooth, homogenous layers (improved buildability and playtime) with fewer clumps than traditional mascaras. The mascaras of the invention are also easily removed with water and experience less flaking or smudging than traditional mascaras.

BRIEF SUMMARY OF THE INVENTION

The present invention relates to a composition comprising:
(a) from about 0.1% to about 30% of at least one liquid fatty substance;
(b) from about 3.3% to about 20% of an emulsifying system comprising (i) from about 0.3% to about 5% of at least one sucrose fatty acid ester, and (ii) from about 1% to about 10% of at least one co-emulsifier;
(c) from about 0.2% to about 10% of at least one viscosity increasing agent;
(d) from about 5% to about 40% of a film forming system comprising (i) from about 1% to about 20% of at least one film forming polymer selected from a styrene/acrylates/ammonium methacrylate copolymer, and (ii) from about 0.2% to about 5% of at least one co-film former; and
(e) from about 30% to about 70% water;
wherein ratio of the sucrose fatty acid ester to the co-emulsifier is between about 1:1 to about 1:20, including all sub-ranges therein, by weight based on the total weight of the composition as a whole, said composition having a viscosity from about 4.7 to about 16.5 Pa*s.

Another embodiment of the invention relates to a method of making up and/or enhancing the appearance of lashes by applying to the lashes the above cosmetic.

Another embodiment of the invention relates to a method of improving at least one property selected from long wear, comfort, playtime, buildability, color intensity, ease of removal, water and/or oil-resistance, shine, adhesion, malleability, transfer resistance and ease of removal properties of mascara by incorporating in said mascara
(b) from about 3.3% to about 20% of an emulsifying system comprising (i) from about 0.3% to about 5% of at least one sucrose fatty acid ester; and (ii) from about 1% to about 10% of at least one co-emulsifier;
(c) from about 0.2% to about 10% of at least one viscosity increasing agent; and
(d) from about 5% to about 40% of a film forming system comprising (i) from about 1% to about 20% of at least one film forming polymer selected from a styrene/acrylates/ammonium methacrylate copolymer, and (ii) from about 0.2% to about 5% of at least one co-film former;
wherein ratio of the sucrose fatty acid ester to the co-emulsifier is between about 1:1 to about 1:20, by weight based on the total weight of the composition as a whole, said composition having a viscosity from about 4.7 to about 16.5 Pa*s.

The composition optionally may include other components appropriate for its intended use such as pigments, preservatives, neutralizers, vitamins, fillers, solvents, fatty substances, and the like.

DETAILED DESCRIPTION OF THE INVENTION

Figure 1:
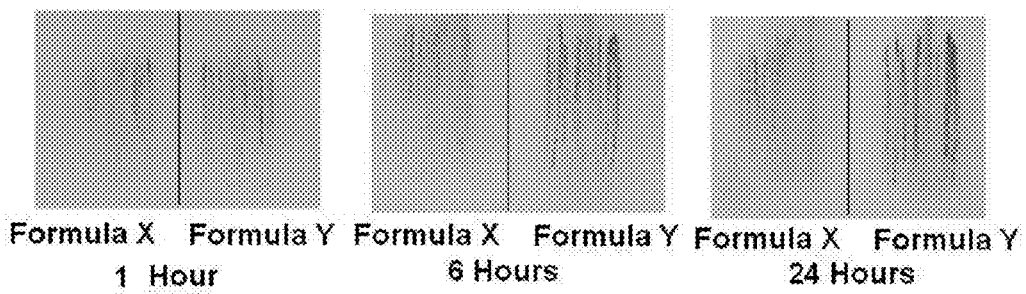
FIG. 1 is an image of blotting paper showing the results of a Sebum Immersion Test Blotter Rubbing comparison between a commercially available mascara (Formula Y) and a mascara according to the invention (Formula X). The fewer the gray traces the more desirable as this evidences less smudging of the mascara.

In the following description of the invention and the claims appended hereto, it is to be understood that the terms used have their ordinary and accustomed meanings in the art, unless otherwise specified. All concentrations are by weight percent on an active basis unless otherwise indicated.

"Aqueous phase" means the phase comprising water as well as such substances of a formulation which, due to their hydrophilic character, can be mixed and/or dissolved and/or dispersed in water. The aqueous phase of the composition according to the invention is advantageously a continuous aqueous phase. A "continuous aqueous phase" means that the composition has a conductivity, measured at 25° C., of greater than 23 microSiemens/cm, the conductivity being measured, for example, using an MPC227 conductimeter from Mettler Toledo and an Inlab 730 conductivity measuring cell.

"Easy removal" means the composition may be substantially removed with a non-harsh remover, such as water, and without excessive rubbing.

"Emulsifier or emulsifying surfactant" is a term of art that is well known to those skilled in the art. It is a compound that has a hydrophilic part and a lipophilic part ("amphiphilic") and facilitates the dispersion of two mutually insoluble phases, in this case the oil and water phases, assisting in the formation of the O/W emulsion. Such compounds do not have an overall electric charge in their working environment (are "non-ionic").

"High color intensity" means dramatic visual impact of the tint, in this instance, the blackness of the lashes.

"Long playtime" means the ability to continually deposit the composition on to the lashes without the composition drying up and/or causing clumps.

"Long wear" compositions as used herein, means the compositions retain at least one property chosen from consistency, texture and color the same over extended period of time (for example 1, 2 or even as long as 8 hours) as viewed by the naked eye. Long wear properties may be evaluated by any method known in the art for evaluating such properties. For example, the consistency, texture and color of the mascara composition may be evaluated immediately following application and these characteristics may then be re-evaluated and compared after an individual has worn the mascara composition for a certain amount of time.

"Oil phase" or "oily phase" means the phase containing the lipophilic, non-ionic compounds that are liquid at room temperature (25° C.) These compounds include one or more mutually compatible non-aqueous fatty substances that are liquid at room temperature, for example organic solvents and oils ("liquid fatty substances") as herein described, and any lipophilic additive that may be present. The oil phase does not include the charged surfactants.

"Tackiness" as used herein refers to the adhesion between two substances. For example, the more tackiness there is between two substances, the more adhesion there is between the substances. Tackiness can be measured and provided in US 2008/0095730, which, to the extent necessary, is herein incorporated by reference in its entirety.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

In a preferred embodiment, the composition of the invention may be in the form of an oil-in-water emulsion (O/W). The O/W emulsions according to the invention comprise an oil phase (or lipophilic phase) dispersed in an aqueous phase. In such emulsions, the aqueous phase is thus the continuous phase of the composition while the oil phase is the dispersed phase of the composition. The oil phase is present in an amount ranging from about 3.4% to about 50%, preferably from about 5% to about 15%, most preferably about 10%, including all ranges and subranges therebetween, by weight relative to the total weight of the composition. The aqueous phase is present in an amount ranging from about 50% to about 97.6%, preferably from about 85% to about 95%, most preferably about 90%, including all ranges and subranges therebetween, by weight relative to the total weight of the composition.

The viscosity of the emulsions, measured at 25% with a Rheomat 180 viscometer at 200 rmp (revolutions per minute) using a No. 4 spindle is preferably greater than or equal to 2.4 Pa*s, preferably from 4.7 to 16.6 Pa*s, most typically 9.5 Pa*s, including all ranges and subranges therebetween. The viscosity is generally measured 10 minutes after switching on the rotation of the spindle.

The pH of the emulsion of the invention at 25° C. ranges from about 6.5 to about 8.5, most preferably about 7.3+/−0.3.

In one embodiment the invention relates to a mascara composition comprising:
 (a) from about 0.1% to about 30% of at least one liquid fatty substance;
 (b) from about 3.3% to about 20% of an emulsifying system comprising (i) from about 0.3% to about 5% of at least one sucrose fatty acid ester; and (ii) from about 1% to about 10% of at least one co-emulsifier;
 (c) from about 0.2% to about 10% of at least one viscosity increasing agent;
 (d) from about 5% to about 40% of at least one film forming system comprising (i) from about 1% to about 20% of at least one film forming polymer selected from a styrene/acrylates/ammonium methacrylate copolymer, and (ii) from about 0.2% to about 5% of at least one co-film former; and
 (e) from about 30% to about 70% water;
 wherein ratio of the sucrose fatty acid ester to the co-emulsifier is between about 1:1 to about 1:20, based on the total weight of the composition as a whole, said composition having a viscosity from about 4.7 to about 16.5 Pa*s.

In another embodiment the invention relates to a mascara composition comprising:
 (a) from about 0.1% to about 30% of at least one liquid fatty substance;
 (b) from about 3.3% to about 20% of an emulsifying system comprising (i) from about 0.3% to about 5% of at least one sucrose fatty acid ester; and (ii) from about 1% to about 10% of at least one co-emulsifier;
 (c) from about 0.2% to about 10% of at least one viscosity increasing agent;
 (d) from about 5% to about 40% of at least one film forming system comprising (i) from about 1% to about 20% of at least one film forming polymer selected from a styrene/acrylates/ammonium methacrylate copolymer, and (ii) from about 0.2% to about 5% of at least one co-film former;

(e) from about 30% to about 70% water; and
(f) from about 1% to about 40% of at least one pigment;
wherein ratio of the sucrose fatty acid ester to the co-emulsifier is between about 1:1 to about 1:20, by weight based on the total weight of the composition as a whole, said composition having a viscosity from about 4.7 to about 16.5 Pa*s.

In a preferred embodiment, the invention relates to an oil-in water emulsion comprising:
(1) an oily phase comprising:
  (a) from about 0.1% to about 30% of at least one liquid fatty substance; and
  (b) from about 3.3% to about 20% of an emulsifying system comprising (i) from about 0.3% to about 5% of at least one sucrose fatty acid ester; and (ii) from about 1.0% to about 10% of at least one co-emulsifier; and
(2) an aqueous phase comprising:
  (c) from about 0.2% to about 10% of at least one viscosity increasing agent;
  (d) from about 5% to about 40% of a film forming system comprising (i) from about 1% to about 20% of at least one film forming polymer selected from a styrene/acrylates/ammonium methacrylate copolymer, and (ii) from about 0.2% to about 5% of at least one co-film former;
  (e) from about 30% to about 70% water; and
  (f) from about 1% to about 40% of at least one pigment;
wherein the oily phase is dispersed in the aqueous phase, said emulsion having a viscosity from about 4.7 to about 16.5 Pa*s, the ratio of the sucrose fatty acid ester to the co-emulsifier is between about 1:1 to about 1:20, and the ratio of the emulsifying system to the final emulsion is between about 1:6 to about 1:30, by weight, all weights being relative to the total weight of the emulsion.

In an embodiment, the liquid fatty substance is selected from cetyl PEG/PPG-10/1 dimethicone, dimethicone (and) dimethiconol, and mixtures thereof.

In another embodiment, the sucrose fatty acid ester is sucrose tristearate.

In an embodiment, the viscosity increasing agent is selected from ammonium polyacryloyldimethyl taurate, ammonium acryloydimethyltaurate/steareth-25 methacrylate crosspolymer, and mixtures thereof.

In an embodiment, the film forming polymer is selected from olefin/acrylate grafted polymer (and) sodium laureth sulfate (and) C12-15 sec-pareth 15 commercially available as SYNTRAN® 108), styrene/acrylates/ammonium methacrylate copolymer (and) sodium laureth sulfate (and) caprylyl glycol (commercially available as SYNTRAN® 5760), acrylates/ethylhexyl acrylate/hema copolymer (and) acrylates/diethylaminoethyl methacrylate/ethylhexyl acrylate copolymer (and) isodeceth-6 (0.149%) (and) caprylyl glycol (and) sodium laureth sulfate (commercially available as SYNTRAN® 5775), and mixtures thereof.

In an embodiment, the co-film former is a polymer selected from divynyldimethicone/dimethicone copolymer (and) C12-13 pareth-23 (and) C12-13 pareth-3.

Another embodiment of the invention relates to method of improving at least one property chosen from long wear, comfort, playtime, buildability, color intensity, ease of removal, water and/or oil-resistance, shine, adhesion, malleability, and transfer resistance and ease of removal properties in a cosmetic composition, said method comprising including in the cosmetic composition:

(b) from about 3.3% to about 20% of an emulsifying system comprising (i) from about 0.3% to about 5% of at least one sucrose fatty acid ester; and (ii) from about 1% to about 10% of a co-emulsifier;
(c) from about 0.20% to about 10% of at least one viscosity increasing agent; and
(d) from about 5% to about 40% of at least one film forming system comprising (i) from about 1% to about 20% of at least one film forming polymer selected from a styrene/acrylates/ammonium methacrylate copolymer, and (ii) from about 0.2% to about 5% of a co-film former;
wherein ratio of the sucrose fatty acid ester to the co-emulsifier is between about 1:1 to about 1:20, by weight based on the total weight of the composition as a whole, said composition having a viscosity from about 4.7 to about 16.5 Pa*s.

Liquid Fatty Substance (a)

The compositions according to the invention contain a liquid fatty substance which may be selected, for example, from organic solvents and volatile and/or non-volatile oils, and mixtures thereof.

Representative suitable solvents include non-polar volatile hydrocarbon-based oils include isodecane and isododecane, and for example, the oils sold under the trade names Isopar™ or Permythyl®. Preferably, the volatile oils have a flash point of at least 40° C.

Other exemplary organic solvents are non-volatile solvents which include polyalphaolefins such as hydrogenated polydecene, hydrogenated C6-14 olefin polymers and polydecene.

Natural oils may also be used so long as they are physiologically acceptable. Such oils include hydrocarbon-based plant oils with a high triglyceride content such as sweet almond oil, avocado oil, olive oil, candlenut oil, vitamin E oil, and the like.

Volatile and non-volatile silicone oils, may also be used. Such oils are described, for example in US 2011/0293550, which to the extent required, is herein incorporated by reference. Suitable silicone oils include, for instance, volatile or non-volatile polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes; and dimethicone fluids having viscosity values of equal to or greater than 300 cst; and mixtures thereof.

In an embodiment, the fatty substance is an oil that is selected from or includes cetyl PEG/PPG-10/1 dimethicone, dimethicone (and) dimethiconol, dimethicone, hydrogenated polyisobutene, PEG-12 dimethicone, dimethiconol and mixtures thereof.

The fatty substance is present in the composition of the invention in an amount of from about 0.1% to about 30%, preferably from about 3% to about 15%, more particularly from about 4% to about 13%, most particularly from about 7% to about 10%, by weight, including all ranges and subranges therebetween, all weights being based on the total weight of the composition.

Emulsifying System (b)

The emulsifying system of the composition according to the invention comprises (i) at least one sucrose fatty acid ester and (ii) at least one co-emulsifier.

The Sucrose Fatty Acid Ester (b)(i)

Sucrose fatty acid esters are known to be emulsion stabilizer and surfactants. See, e.g., Sucrose Fatty Acid Esters. Non-limiting examples of sucrose fatty acid esters useful in the invention include, for example, sucrose cocoate sucrose laurate (and) aqua (and) alcohol (Surfhope® C-1215 commercially available from Mitsubishi-Kagaku), sucrose laurate, sucrose myristate, sucrose palmitate, sucrose polystearate, sucrose tristearate, sucrose distearate, sucrose stearate, sucrose dilaurate, sucrose hexaerucate, sucrose oleate, sucrose pentaerucate, sucrose polybehenate, sucrose polycottonseedate, sucrose polylaurate, sucrose polylinoleate, sucrose polypalmate, sucrose polyoleate, sucrose polysoyate, sucrose ricinoleate, sucrose tetraisostearate, sucrose tribehenate, sucrose hexaoleate/hexapalmitate/hexastearate, sucrose hexapalmitate, sucrose trilaurate, and mixtures thereof.

Preferred sucrose fatty acid esters include sucrose laurate (and) aqua (and) alcohol, sucrose laurate, sucrose myristate, sucrose palmitate, sucrose polystearate, sucrose tristearate, sucrose distearate, sucrose stearate, and mixtures thereof, all of which are commercially available from Mitsubishi-Kagaku under the tradename Surfhope® C. The sucrose fatty acid ester may be used, for example, as a mixture with other ingredients, for example alcohol, in the form of products sold, for example, by Mitsubishi-Kagaku under the trade name Surfhope® C. Particularly preferred sucrose fatty acid esters include sucrose stearate, sucrose distearate, sucrose tristearate, and mixtures thereof, and most particularly sucrose tristearate.

The sucrose fatty acid ester is present in the composition of the invention in an amount of from about 0.3% to about 5%, preferably from about 1% to about 4%, more preferably about 2.6%, including all ranges and subranges therebetween, by weight, all weights being based on the total weight of the composition.

Co-emulsifier (b)(ii)

Preferably, the sucrose fatty acid ester according to the invention is used with a co-emulsifier. Non-liming examples of co-emulsifiers include a glyceryl ester of a $C_{14}$-$C_{20}$ fatty acid (preferably a stearate), such as for example PEG-200 glyceryl stearate, glycerol stearate, glyceryl stearate citrate, and mixtures thereof. Other co-emulsifiers include polysorbate 61, stearyl alcohol, and mixtures all of the foregoing co-emulsifiers.

The co-emulsifier is present in the compositions of the invention in an amount ranging from about 1% to about 10%, preferably from about 2% to about 7%, more particularly, from about 2.5% to about 4%, most typically about 3%, including all ranges and subranges therebetween, by weight, relative to the total weight of the compositions.

Viscosity Increasing Agent ("Thickener" or "Rheology Increasing Agent") (c)

Representative viscosity increasing agents include thickening agents and gelling agents. The viscosity increasing agent(s) that may be useful in the practice of embodiments of the disclosure include those conventionally used in cosmetics such as polymers of natural origin and synthetic polymers.

Viscosity increasing agents may be selected from, for example vegetable gums, liposoluble/lipodispersible polymers, salts, and mixtures thereof. Preferably the viscosity increasing agents are not waxes.

Representative viscosity increasing agents that may be used in the practice of embodiments according to the disclosure may be chosen from nonionic, anionic, cationic, and amphoteric polymers, including acrylate-based polymers, polysaccharides, polyamino compounds, amphiphilic polymers, and other viscosity modifiers such as cellulose-based thickeners (e.g., hydroxyethylcellulose, hydroxypropylcellulose, carboxymethylcellulose, cationic cellulose ether derivatives, quaternized cellulose derivatives, etc.), guar gum and its derivatives (e.g., hydroxypropyl guar, cationic guar derivatives, etc.), gums such as gums of microbial origin (e.g., xanthan gum, scleroglucan gum, etc.), and gums derived from plant exudates (e.g., gum arabic, ghatti gum, karaya gum, gum tragacanth, carrageenan gum, agar gum and carob gum), pectins, alginates, and starches, cross-linked homopolymers of acrylic acid or of acrylamidopropane-sulfonic acid, associative polymers, non-associative thickening polymers, water-soluble thickening polymers, and mixtures of these.

Other non-limiting examples of such agents include glycerol behenate, polyethylene and copolymers thereof such as PEG-150 distearate, magnesium stearate, synthetic polymers such as polyacrylic acid (available commercially as Carbomers) and acrylates copolymers such as sodium polyacrylate and polyacryloyldimethyl taurate, and mixtures of these.

In an embodiment, the viscosity increasing agent is selected from ammonium polyacryloyldimethyl taurate, ammonium acryloydimethyltaurate/steraeth-25 methacrylate crosspolymer, sorbitol/sebacic acid copolymer behenate, ethylenediamines/stearyl dimer dilinoleate copolymer, and mixtures thereof.

In a particular embodiment, the viscosity increasing agent is selected from ammonium polyacryloyldimethyl taurate, sorbitol/sebacic acid copolymer behenate ethylenediamines/stearyl dimer dilinoleate copolymer, and mixtures thereof.

The viscosity increasing agent is present in the composition of the invention in an amount of from about 0.2% to about 10%, preferably from about 0.5% to about 6.0%, more particularly from about 1% to about 4%, preferably from about 1.9% to about 2.5%, by weight, including all ranges and subranges therebetween, all weights being based on the total weight of the composition.

Film-forming Polymers (d)(i)

As used herein, the terms "film-forming polymer," "film former," "film-forming agent" and variations thereof mean a polymer capable of, by itself or in the presence of an auxiliary film-forming agent, forming a continuous film that adheres to a support and especially to keratin materials, for instance the eyelashes.

The film-forming polymers that may be used in the cosmetic compositions disclosed herein include, for example, acrylate copolymers, styrene/acrylate copolymers, acrylaminde/acrylate copolymers, polyurethanes, derivatives thereof and mixtures thereof.

In accordance with various exemplary embodiments, acrylate copolymers may be chosen from copolymers comprising two or more monomers chosen from acrylic acid, methacrylic acid, and their simple esters, for example, lower alkyl esters such as methyl, ethyl, and ethylhexyl esters.

By way of non-limiting example only, acrylate copolymers may be chosen from ammonium acrylates copolymers, ethyl acrylates copolymers, acrylates/ethylhexylacrylate copolymers, acrylates/octylacrylates copolymers, alkyl (meth)acrylates copolymers, acrylates/$C_{12}$-$C_{22}$ alkylmethacrylate copolymers, ethylacrylate/methacrylic acid copolymer, and t-butyl acrylate/ethyl acrylate/methacrylic acid copolymer. Exemplary commercial acrylate copolymers include, but are not limited to, ALLIANZ™ OPT sold by Ashland Specialty Ingredients; COVACRYL A15 and COVACRYL E14 sold by Sensient Cosmetic Technologies LCW; DAITOSOL 4000 SJT, DAITOSOL 5000 AD, DAITOSOL 5000 SJ, KOBOGUARD® 50A, and KOBOGUARD® 50N sold by Kobo Products, Inc.; DERMACRYL® AQF, YODOSOL 32A707, YODOSOL GH15, YODOSOL GH32, YODOSOL GH33, YODOSOL GH34, YODOSOL GH35, YODOSOL GH800, and YODOSOL GH810 sold by AkzoNobel; LUVIFLEX® SOFT, LUVIMER® 36D, and LUVIMER® 100P sold by BASF; and NEOCRYL® XK-90 sold by Neoresins, Inc.

The film forming agent may also be chosen from polyacrylates such as polyacrylate-21, and polyacrylate-15, and acrylates copolymer.

The film-forming agent may also be chosen from latex film forming polymers such as polyacrylate latex, polyurethane latex, and their copolymers.

Suitable examples of latex polymers for use in the present invention are ethylhexyl acrylate/hema copolymer (and) acrylates/diethylaminoethyl methacrylate/ethylhexyl acrylate copolymer (Syntran® PC 5775), styrene/acrylates/ammonium methacrylate copolymer (Syntran® 5760, Syntran® 5009, Syntran® PC5620), polyacrylate-21 (and) acrylates/dimethylaminoethyl methacrylate copolymer (Syntran® PC5100, Syntran® PC5776, Eudragit® E 100, Jurymer ET-410C), styrene/acrylates/ammonium methacrylate copolymer (Syntran® 5009 CG), olefin/acrylate grafted polymer (and) sodium laureth sulfate (and C12-15 SEC-pareth 15 (Syntran® EX108), acrylates copolymer (Aculyn® 33A Polymer, Avalure® Ace 210/120/315 Acrylic Copolymer, Carbopol® Aqua SF-1 Polymer, Daitosol® 500 AD, Coatex® Co 633, Eliclear® 380/700/4U, Eudragit® L 100, Joncryl® 85, Luviflex® Soft), acrylates/ethylhexyl acrylate copolymer (Daitosol® 5000SJ, Daitosol® 4000SJT, MJA PS34-21, SDP-001). The Syntran® polymers are commercially available from the supplier Interpolymer Corp.

Suitable examples of latex polymers are polyurethane-35, polyurethane-35, and polyurethane-35.

In an embodiment, the latex polymer is an acrylate latex polymer, in particular styrene/acrylate copolymers.

Other non-limiting examples of commercially available styrene/acrylate copolymers include, but are not limited to, DAITOSOL® 5000 STY sold by Kobo Products, Inc.; JONCRYL® 77 sold by BASF; NEOCRYL® BT-62 sold by Neoresins, Inc.; RHOPLEX™ P-376 and UCAR™ DL 432S sold by Dow Chemical Company; and YODOSOL GH41 and YODOSOL GH840 sold by AkzoNobel.

In further exemplary embodiments, acrylamide/acrylate copolymers may be chosen from acrylic acid/ethyl acrylate/t-butyl acrylamide copolymer, acrylates/octylacrylamide copolymer, and octylacrylamide/acrylates/methacrylates copolymer. Exemplary commercial acrylamide/acrylate copolymers include, but are not limited to AMPHOMER® LV-71 and DERMACRYL® 79 sold by AkzoNobel and ULTRAHOLD® STRONG sold by BASF.

According to additional exemplary embodiments, polyurethanes may be chosen from polyurethane-32, polyurethane-34, and polyurethane-35. Exemplary commercial polyurethanes include, but are not limited to, products sold by Bayer under the trade name BAYCUSAN®, such as BAYCUSAN® C1000, BAYCUSAN® C1001, BAYCUSAN® C1003, and BAYCUSAN® C1004.

In at least one exemplary embodiment, the latex film former may be chosen from blends comprising a combination of latex film formers, including, for example, a blend of any of the above-mentioned film formers. By way of non-limiting example, a latex film forming blend useful according to the disclosure may comprise (1) at least one random styrene acrylate copolymer or derivatives thereof, and at least one acrylate copolymer or derivatives thereof, or (2) at least two random styrene acrylate copolymers or derivatives thereof.

In an embodiment the film former is selected from styrene/acrylates/ammonium methacrylate copolymers sold by Interpolymer Corporation, in particular SYNTRAN® 5760 (styrene/acrylates/ammonium methacrylate copolymer (and) sodium laureth sulfate (and) caprylyl glycol); SYNTRAN® 5775 (acrylates/ethylhexyl acrylate/hema copolymer (and) acrylates/diethylaminoethylmethacrylate/ethylhexyl acrylate copolymer (and) isodeceth-6 (and) caprylyl glycol (and) sodium laureth sulfate); SYNTRAN® Ex 108 (olefin/acrylate grafted polymer (and) sodium laureth sulfate (and) C12-15 SEC-pareth 15); and SYNTRAN® 108 GC (olefin/acrylic grafted emulsion). Most particularly, the firm former is SYNTRAN® 5775 (acrylates/ethylhexyl acrylate/hema copolymer (and) acrylates/diethylaminoethylmethacrylate/ethylhexyl acrylate copolymer (and) isodeceth-6 (and) caprylyl glycol (and) sodium laureth sulfate).

According to at least certain exemplary embodiments of the disclosure, the at least one latex film former may be chosen from those having a glass transition temperature (Tg) ranging from about −15° C. to about 90° C., such as from about 0° C. to about 50° C.

In accordance with various exemplary embodiments, the at least one film former may be present in the cosmetic composition in an amount, or a combined amount when more than one film former is used, ranging from about 1% to about 20%, typically from about 3% to about 12%, more typically from about 7% to about 10%, more particularly from about 7% to about 8%, including all ranges and subranges therebetween, by weight, relative to the total weight of the compositions.

Co-film Former (d)(ii)

In addition to at least one film former, the compositions preferably also include a co-film former, which may be selected, for example, from any of the foregoing film-forming agents. In a particular embodiment, the co-film former is selected from divinyldimethicone/dimethicone copolymer (and) C12-13 pareth-3 (and) c-12-13 pareth-23, VP/Eicosene copolymer, and mixtures thereof.

In accordance with various exemplary embodiments, the co-film former may be present in the cosmetic composition in an amount ranging from about 0.2% to about 5%, preferably from about 1% to about 3%, and most preferably from about 2% to about 2.5%, including all ranges and subranges therebetween, by weight relative to the total weight of the compositions.

Coalescent and/or Plasticizer (Optional)

In addition to at least one latex film former, the compositions may, in at least certain exemplary embodiments, optionally further comprise at least one coalescent and/or plasticizer. It is known that inclusion of a coalescent agent promotes the coalescence of polymer particles in an aqueous dispersion, and inclusion of a plasticizer makes it possible to plasticize a polymer in an aqueous dispersion. Any coalescent and/or plasticizer may be used, and one of skill in the art will be able to choose an appropriate coalescent and/or plasticizer with little or no routine experimentation based on, for example, the type of cosmetic composition being formulated and the desired properties thereof.

Optional coalescents and/or plasticizers useful according to various exemplary embodiments of the disclosure include, but are not limited to, those disclosed in U.S. Pat. No. 6,372,201. By way of example only, optional plasticizers may be chosen from tributyl citrate, texanol ester alcohol, diisobutyl adipate, the ester of tertbutyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, and mixtures thereof. By way of example only, optional coalescents may be chosen from butylene glycol, caprylyl glycol, propylene glycol n-butyl ether, dipropylene glycol dibenzoate, dipropylene glycol dimethyl ether, propylene glycol methyl ether acetate, propylene glycol propyl ether, methyl lactate, ethyl lactate, isopropyl lactate, and mixtures thereof. In an embodiment the optional coalescent is selected from butylene glycol, caprylyl glycol, and mixtures thereof.

In accordance with various exemplary embodiments, the coalescents and/or plasticizers may be present in the cosmetic composition in an amount ranging from about 0.1% to about 10%, preferably from about 1% to about 4%, most preferably from about 2%, including all ranges and subranges therebetween, by weight relative to the total weight of the compositions.

Emollients/Moisturizers (Optional)

In an embodiment, the compositions of the invention include one or more emollient/moisturizer. These compounds hydrate the lashes and also provide a "wet" texture and shiny look. Without limitation, useful emollients include, for example, carnauba wax, beeswax, mineral oil, almond oil, castor oil, sesame oil, hydrogenated polyisobutene, butylene glycol dicaprylte dicaprate (commercially available from Sasol as Myglyol®), and the like, and mixtures thereof. PEG-12 dimethicone as well as dimethicone (and)dimethicol may also be used as emollients. Preferred emollients include hydrogenated polyisobutene, butylene glycol dicaprylte dicaprate, PEG-12 dimethicone, dimethicone (and)dimethicol and mixtures thereof.

Water (e)

The compositions for the invention also comprise water in an amount ranging from about 30% to about 70%, preferably from about 45% to about 60%, most typically from about 53% about 59%, including all ranges and subranges therebetween, by weight, relative to the total weight of the compositions.

The aqueous phase may include at least one organic solvent that is water-miscible. Non-limiting examples of suitable organic solvents include $C_{1-4}$ alkanols, such a sethanol and isopropanol; glycerol; glycols and glycol ethers such as 2-butoxyethanol, propylene glycol, butylene glycol, monomethyl ether of propylene glycol, monoethyl ether and monomethyl ether of diethylene glycol, aromatic alcohols such as benzyl alcohol and phenoxyethanol; analogous products and mixtures of the foregoing products.

Other solvents include caprylic/capric acid triglycerides (such as those sold under the trade name Miglyol®.

In a particular embodiment the solvent is butylene glycol, phenoxy ethanol, and mixtures thereof.

The compositions of the invention may comprise a solvent in an amount ranging from about 0.1% to about 20%, preferably from about 1% to about 5%, particularly about 2%, including all ranges and subranges therebetween, by weight, relative to the total weight of the compositions.

Pigments (f)(Optional)

The cosmetic composition of the invention may optionally include at least one pigment (or dyestuff). Suitable pigments/dyes include, but are not limited to, pulverulent dyestuffs, liposoluble dyes, and water-soluble dyes.

The pulverulent dyestuffs may, for instance, be chosen from pigments and nacres. Useful pigments include titanium dioxide, zirconium oxide, zinc oxide, cerium oxide, iron oxide, chromium oxide, manganese violet, ultramarine blue, chromium hydrate, and ferric blue. Non-limiting examples of organic pigments include carbon black, pigments of D&C type, and lakes based on cochineal carmine, barium, strontium, calcium, and aluminum.

The nacres which may be used include, for example, colored nacreous pigments such as titanium mica with iron oxides, titanium mica with ferric blue or chromium oxide, titanium mica with an organic pigment chosen from those listed above, and nacreous pigments based on bismuth oxychloride.

In an embodiment the pigment is iron oxides.

The at least one pigment/dyestuff may be present in the cosmetic composition in an amount ranging from about 1% to about 40%, more particularly from about 5% to about 20%, particularly about 10%, including all ranges and subranges therebetween, by weight, relative to the total weight of the compositions.

Fillers (g) (Optional)

The cosmetic composition disclosed herein may also comprise at least one filler commonly used in the art in cosmetic compositions. The fillers may be lamellar or non-lamellar, inorganic or organic particles. Representative, non-limiting examples of these ingredients include mica, silica, kaolin, iron oxides, titanium dioxide, polyamide powders, polyamide powders, for instance Nylon® (Orgasol from Atochem), poly-alanine powders, polyethylene powders, tetrafluoroethylene polymer powders, for instance polytetrafluoroethylene (Teflon®), lauroyllysine, starch, boron nitride, hollow polymer microspheres such as those of polyvinylidene chloride/acrylonitrile, for instance Expancel® (Nobel Industrie), acrylic powders such as Polytrap® (Dow Corning), polymethyl methacrylate particles and silicone resin microbeads (for example, Tospearls® from Toshiba), methylsilanol/silicate crosspolymer, precipitated calcium carbonate, magnesium carbonate, magnesium hydrocarbonate, hydroxyapatite, hollow silica microspheres (Silica Beads® from Maprecos), glass or ceramic microcapsules, metal soaps derived from organic carboxylic acids containing from 8 to 22 carbon atoms, preferably from 12 to 18 carbon atoms, for example, zinc stearate, magnesium stearate, lithium stearate, zinc laurate, or magnesium myristate.

The fillers, if present, are present in amounts generally ranging from about 0.1% to about 25%, such as from about 1% to about 20% by weight, relative to the total weight of the composition, including all ranges and subranges therebetween.

Fibers (Optional)

In some embodiments, the cosmetic composition may further comprise at least one fiber, which may improve the lengthening effect of the composition. The fibers useful in the present disclosure may be chosen from rigid or non-rigid fibers and may be of natural or synthetic origin. Natural fibers include, but are not limited to, cotton, silk, wool, and other keratin fibers. Synthetic fibers include, but are not limited to, polyester, rayon, nylon, and other polyamide fibers. In some embodiments, fibers may be made of non-rigid fibers such as polyamide (Nylon®) fibers, or rigid fibers such as polyimide-amide fibers, for instance, those sold under the trade name "Kermel" and "Kermel Tech" by Rhodia, or poly(p-phenyleneterephthalamide) (or aramid) fibers sold especially under the name Kevlar® by DuPont de Nemours.

The fibers, if present, may be present in the cosmetic composition in an amount generally ranging from about 0.01% to about 10% by weight, relative to the total weight of the composition, including all ranges and subranges therebetween.

Further Additional Components (Optional)

The compositions of the present invention can also include any additional ingredient or additive usually used in the field of mascara compositions.

For example, these may be chosen from, for example, solvents, dispersants, antioxidants (such as pentaerythrityl tetra-di-t-butyl hydroxyhydrocinnamate), preservatives, fragrances, additional thickeners or texturizers, liquid lipids/oils, additional viscosity modifiers, additional film formers, sunscreen agents, additional pigments/colorants/dyes, silica, clays, additional humectants and moisturizing agents, additional emulsifying agents (e.g. sorbitan oleate), additional structuring agents and fillers, additional surfactants, shine agents, conditioning agents, cosmetically, dermatologically and pharmaceutically active agents, vitamins, plant extracts, additional film-formers, coalescents/plasticizers, pH modifiers/neutralizing agents, stabilizers, and mixtures thereof. A non-exhaustive listing of such ingredients is found in U.S. Pat. No. 7,879,316, the entire content of which is hereby incorporated by reference. Additional examples of additives may be found in the *International Cosmetic Ingredient Dictionary and Handbook* ($9^{th}$ ed. 2002, and subsequent editions).

The compositions of the invention are preferably devoid of waxes, but include a very small amount (up to about 5% of wax).

One of skill in the art will be able to select appropriate types and amounts of additional cosmetic ingredients, based on, for example, the type of cosmetic composition being formulated and the desired properties thereof. Any one or more of the additional components set forth above may be included in the compositions.

The surfactants that may be employed as additional agents may be chosen from anionic, cationic, nonionic and amphoteric surfactants.

The shine agents may be chosen from silicones, alkoxylated silicones, oils, ethoxylated oils, fats, esters, transesters, hydrocarbons, quats and mixtures thereof.

Non-limiting examples of shine agents include Amodimethicone, Dimethicone, Dimethiconol, Cyclemethicone, Phenyltrimethicone, Aminopropyl Phenyltrimethicone, Trimethyl Pentaphenyl Trisiloxane, Cetyl Dimethicone, Alkyl Dimethicone, Potassium Dimethicone PEG-7 Pantheyl Phosphate, Olive oil, Jojoba oil, Apricot oil, Avocado oil, Castor oil, Lanolin, Squalane, Capric/Caprylic Triglyceride, Octyl Palmitate, Isopropyl Palmitate, Isopropyl Myristate, Mineral oil, Petrolatum, Polyquaternium-4, Polyquaternium-11, Behentrimonium Methosulfate, Benetrimonium Chloride and mixtures thereof.

Specific examples of additional ingredients include oils, for example dimethicone and dimethiconol, vitamins, for example vitamin E, fillers, for example Perlite, additional thickeners and/or stabilizers, for example ammonium acryloyldimethyltaurate/steareth-25 methacrylate crosspolymer, sodium acrylates/sodium acryloyldimethyl taurate copolymer/sodium acrylate/sodium acryloyldimethyl taurate copolymer (and) isohexadecane (and) polysorbate 80, disodium EDTA, tetrasodium EDTA, potassium sorbate, sodium dehydroacetate, neutralizers such as aminomethyl propane-diol and citric acid, preservatives, for example caprylyl glycol and phenoxyethanol, additional plasticizers/film formers, for example PeG-12 dimethicone, and solvents such at butylene glycol.

If present in the composition, these additives may constitute from 2% to 30%, typically from about 5% to about 15%, and more typically about 7%, including all ranges and subranges therebetween, by weight relative to the total weight of the composition.

Cosmetic Methods

In an embodiment according to the invention, the compositions comprising an emulsifying system including at least one sucrose fatty acid ester, a co-emulsifier, a viscosity increasing agent and a film forming polymer can impart thickening and volumizing properties to the lashes, while also lengthening the eyelashes with desirable lash separation and resistance to clumping. Accordingly, another embodiment of the invention provides a method of making up/or enhancing the appearance of eyelashes by applying to the lashes topically the composition of the present invention in a sufficient amount to make up the lashes. The compositions may be applied to the eyelashes as needed, preferably once or twice daily, and then allowed to dry before subjecting to contact such as with clothing or other objects.

"Volume," as used herein, refers to the apparent build-up of the composition on the lashes. As volume increases each eyelash is defined and stands out to the eye, creating the desirable impression of longer and fuller lashes. A composition that produces increased thickness is considered to have good volume properties. Volume may be evaluated by any method known in the art for evaluating such properties. By way of example only, volume may be evaluated by a test involving first measuring the thickness of human eyelashes or hair. The composition is then applied to the eyelashes or hair. After a period of drying, the thickness of the eyelashes or hair is once again measured. The difference in volume from before and after treatment is then determined. Further, these characteristics may be evaluated with respect to other compositions, such as commercially available compositions.

The compositions according to various exemplary embodiments of the invention may also have improved and/or increased ease of removability, relative to similar compositions not having the at least one sucrose fatty acid ester, a co-emulsifier, a viscosity increasing agent and a film forming polymer as described herein. In various embodiments, ease of removability relates to ease of removing the composition from the lashes with warm (e.g. about 50° C. or higher) water. Optionally, conventional cleansing agents such as soap or make-up remover may also be used.

As such, the disclosure also relates to methods of improving or increasing the ease of removability of mascara compositions by incorporating into said mascara compositions at least one sucrose fatty acid ester, a co-emulsifier, a viscosity increasing agent and a film forming polymer, such as at least one latex film former, as described herein.

Another embodiment of the invention relates to a method of improving at least one property selected from long wear, comfort, playtime, buildability, color intensity, ease of removal, water and/or oil-resistance, shine, adhesion, malleability, transfer resistance and ease of removal properties by incorporating in said mascara at least one sucrose fatty acid ester, a co-emulsifier, a viscosity increasing agent and a film forming polymer as described herein.

Unless otherwise indicated, all numbers used in the specification and claims are to be understood as being modified in all instances by the term "about," whether or not so stated. It should also be understood that the precise numerical values used in the specification, including the examples and claims, form additional embodiments of the invention, and are intended to include any ranges which can be narrowed to any to end points disclosed within the exemplary ranges and values provided. Efforts have been made to ensure the accuracy of the numerical values disclosed. However, any measured value can inherently contain certain errors resulting from the standard deviation found in its respective measuring technique.

EXAMPLES

The following Examples are intended to be non-restrictive and explanatory only, with the scope of the invention being defined by the claims.

Method of Preparation:

The mascara compositions described below were prepared by mixing, independently, the components set forth in Table 1 below, as follows:

1. While heating to 70° C., combined phase 1 ingredients in the main kettle and ground pigments at high shear for 1 hour.
2. Combined phase 2 ingredients in a support kettle and mixed under heat until the solids were dissolved.
3. Added phase 2 mixture to the main kettle when both reached 70° C. and homogenized for 20 minutes at high shear.
4. Started cooling and paddle mixed. When batch reached 60° C., added phase 3 ingredients.
5. Continued the slow mixing until batch reached room temperature.

TABLE 1

Examples 1-2

| INCI US Name | Concentration/Component Ex 1 | Ex 2 |
|---|---|---|
| ACRYLATES/ETHYLHEXYL ACRYLATE/HEMA COPOLYMER (EX1: 6.055%, EX2: 6.22%) (and) ACRYLATES/DIETHYLAMINOETHYL METHACRYLATE/ETHYLHEXYL ACRYLATE COPOLYMER (EX1: 1.499%, EX2: 1.54%) (and) ISODECETH-6 (EX1: 0.117%, EX2: 0.12%) (and) CAPRYLYL GLYCOL (and) SODIUM LAURETH SULFATE (EX1: 0.097%, EX2: 0.1%) (Syntran ® 5775) (Phase 3) | 7.768 (d)(i) w/out cap glyclol | 7.980 (d)(i) w/out cap glyclol |
| POLYSORBATE 61 | 1.76% (b) (ii) | 1.76% (b) (ii) |
| AMMONIUM POLYACRYLOYLDIMETHYL TAURATE (Phase 1) | 0.244% (c) | 0.244% (c) |
| BUTYLENE GLYCOL (Phase 1) | 2.195% | 2.2% |
| CAPRYLYL GLYCOL (Phase 1) | 0.397% | 0.4% |
| AMINOMETHYL PROPANEDIOL (Phase 1) | 0.7% | 0.7% |
| IRON OXIDES (Phase 1) | 10% | 10% |
| PHENOXYETHANOL (Phase 1) | 0.895% | 0.9% |
| SORBITOL/SEBACIC ACID COPOLYMER BEHENATE | 5% (c) | 5% (c) |
| DISODIUM EDTA (Phase 1) | 0.099% | 0.099% |
| DIVINYLDIMETHICONE/DIMETHICONE COPOLYMER (1.2%) and C12-13 PARETH-3 (0.04%) and C12-13 PARETH-23 (0.056%) (Phase 3) | 1.296% (d)(ii) | 1.296% (d)(ii) |
| HYDROGENATED POLYISOBUTENE | 2.500% (a) | 2.500% (a) |
| CITRIC ACID (Phase 1) | 0.3% | 0.3% |
| DIMETHICONE (Phase 2) | 0.88% (a) | 0.88% (a) |
| PEG-12 DIMETHICONE (Phase 2) | 1% (a) | 1% (a) |
| ETHYLENEDIAMINE/STEARYL DIMER DILINOLEATE COPOLYMER | 1.735% (c) | 1.735% (c) |
| SUCROSE TRISTEARATE | 2.64% (b) (i) | 2.64% (b) (i) |
| DIMETHICONOL (Phase 2) | 0.12% (a) | 0.12% (a) |
| T-BUTYL ALCOHOL (Phase 1) | 0.0065% | 0.0065% |
| STEARYL ALCOHOL | 1.21% (b) (ii) | 1.21% (b) (ii) |
| POTASSIUM SORBATE (Phase 3) | 0.195% | 0.2% |
| SILICA (Phase 2) | 2% | 2% |
| WATER (Phase 1) | 55.85% (e) | 55.269% |
| SODIUM DEHYDROACETATE (Phase 1) | 0.2% | 0.2% |
| PENTAERYTHRITYL TETRA-DI-T-BUTYL HYDROXYHYDROCINNAMATE (Phase 2) | 0.005% | 0.005% |
| VP/EICOSENE COPOLYMER | 1% (d) (ii) | 1% (d) (ii) |

TABLE 1-continued

Examples 1-2

| INCI US Name | Concentration/Component | |
| --- | --- | --- |
| | Ex 1 | Ex 2 |
| SODIUM ACRYLATE/SODIUM ACRYLOYLDIMETHYL TAURATE COPOLYMER / SODIUM ACRYLATE/SODIUM ACRYLOYLDIMETHYL TAURATE COPOLYMER (0.188%) and ISOHEXADECANE (0.113%) and POLYSORBATE 80 (0.0375%) | | 0.3385% |
| SORBITAN OLEATE | | 0.0125% |
| Total (including VI): | 100% | 99.95% |

Comparative Testing
Wear Tests:
Application of Mascara Compositions to Test Lashes:

Test lashes were prepared for the below tests as follows. The specified mascara compositions were applied onto fake lashes, 3×10 strokes for each lash, with the mascara brush being dipped after each set of 10 strokes. Lashes were allowed to dry for 1 hour before testing.

In the following tests, the inventive composition of Example 1 is referred to as Formula X. Comparative Formula Y is a commercially available mascara having the composition including the ingredients in Table 2 below.

TABLE 2

| Formula Y | |
| --- | --- |
| INCI US Name | Concentration % |
| WATER | 47.93 |
| PHENOXYETHANOL | 0.5 |
| DIMETHICONE | 0.13 |
| GLYCERIN | 2 |
| ACACIA SENEGAL GUM | 3.39 |
| HYDROXYETHYLCELLULOSE | 0.89 |
| IRON OXIDES | 7.14 |
| POTASSIUM CETYL PHOSPHATE | 8.27 |
| BEESWAX | 4.37 |
| COPERNICIA CERIFERA (CARNAUBA) WAX | 3.45 |
| PARAFFIN | 13.82 |
| STEARETH-20 | 0.5 |
| CETYL ALCOHOL | 2 |
| SODIUM POLYMETHACRYLATE | 1 |
| POLYQUATERNIUM-10 | 0.1 |
| PEG/PPG-17/18 DIMETHICONE | 0.5 |
| PHENYL ETHYL ALCOHOL | 0.5 |

The scale used for visual evaluation of samples was as follows:

| Scale for Blotter Rubbing | |
| --- | --- |
| 0 | No Trace |
| 1 | Imperceptible Trace |
| 2 | Few Gray Traces |
| 3 | Some Gray Traces |
| 4 | Gray Traces |
| 5 | Visible Gray Traces |
| 6 | Very Visible Gray Traces |
| 7 | Some Visible Gray Traces |
| 8 | Visible Black Traces |
| 9 | Substantial Black Visible Traces |

Squalane (Sebum) Immersion Test

Each lash sample was immersed in sebum for 1 hour then rubbed 10 times (12 RPMS) on a blotter with a pendulum motion. The sample was then returned to the sebum and the process was repeated at 6 and 24 hours. The traces on the blotter were evaluated visually. The blotters were photographed and reproduced as FIG. 1 below.

The results of the test are shown in Table 3 below.

TABLE 3

Sebum Immersion Test Blotter Rubbing Results

| Time Point | Commercial mascara (Formula Y) Treated lashes (no sucrose fatty acid ester) | Formula X (Ex 1) Treated lashes (sucrose fatty acid ester) |
| --- | --- | --- |
| 1 hour | 4-Gray Traces | 3-Some Gray Traces |
| 6 hours | 5-Visible Gray Traces | 4-Gray Traces |
| 24 hours | 6-Very Visible Gray Traces | 3-Some Gray Traces |

As shown in Table 3 and FIG. 1, the compositions of the invention containing a sucrose fatty acid ester (Formula X) are less likely to streak or transfer (retain same number of gray traces over time) than the comparator mascara (Formula Y), which does not include a sucrose fatty acid ester.

Water Immersion Test

Each lash sample was placed under 25° C. running water for 1 minute. The sample was then rubbed 10 times (at 12 RPMS) on a blotter with a pendulum motion. Each lash sample was then immersed in water for 1 hour, followed by rubbing 10 times on a blotter in a pendulum motion (at 12 RPMS). The lash samples were then once again immersed in water for 6 hour and 24 hour intervals and rubbed on blotter paper each time following the procedure as above. The traces on the blotter were evaluated visually.

The results of the water immersion test are shown in Table 4 below.

TABLE 4

Water Immersion Test Blotter Rubbing Results

| Time Point | Commercial Formula Y mascara Treated lashes | Formula X Treated Lashes |
| --- | --- | --- |
| 1 minute | 8-Visible Black Traces | 3-Some Gray Traces |

TABLE 4-continued

Water Immersion Test Blotter Rubbing Results

| Time Point | Commercial Formula Y mascara Treated lashes | Formula X Treated Lashes |
|---|---|---|
| 1 hour | *N/A | 5-Visible Gray Traces |
| 6 hours | *N/A | 4-Gray Traces |
| 24 hours | *N/A | 3-Some Gray Traces |

*No sample remaining on the lashes as it had been washed off during the water immersion. Therefore there was little/no sample that could be transferred to blotting paper upon rubbing.

Figure 2:
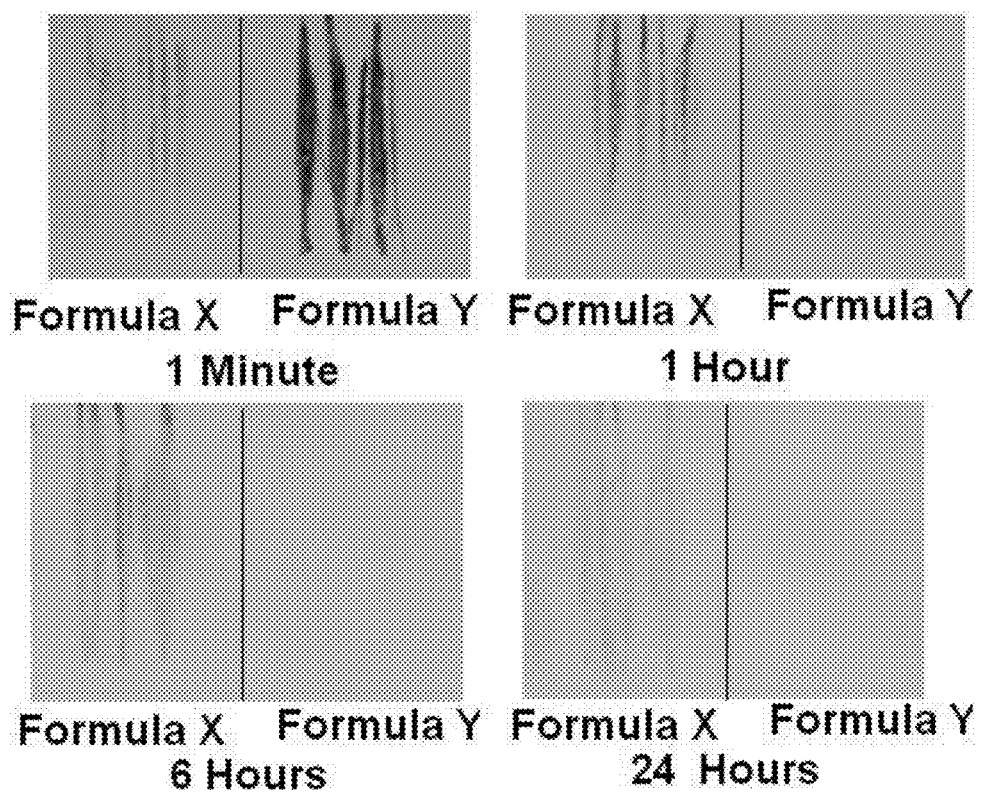
FIG. 2 is an image of blotting paper showing the results of a Water Immersion Test Blotter Rubbing comparison between a commercially available mascara (Formula Y) and a mascara according to the invention (Formula X). This figure shows that the mascara's of the invention are more water resistant than the commercially-available mascara comparator.

As shown in Table 4 and FIG. 2, the compositions of the invention containing a sucrose fatty acid ester are much less likely to rub off after water immersion (that is, they are more water-resistant) than the comparator mascara, which does not include a sucrose fatty acid ester.

Dry Sample/Flake Test

Samples of fake lashes coated as above-described with either Formula Y or the composition of the invention (Formula X) were allowed to dry. After drying, each sample was rubbed with a dry brush 30 times and the debris was collected on adhesive paper and evaluated visually.

The scale used for the visual evaluation of this test was as follows:

Dry Rubbing Scale for Flake Test:

| Dry Rubbing Scale for FlakeTest: | |
|---|---|
| 0 | Nothing |
| 1 | Practically Nothing |
| 2 | Few Grains |
| 3 | Some Grains |
| 4 | Grains |
| 5 | High Number of Grains |
| 6 | Very High Number of Grains |

The results of this test are shown in Table 5 below.

TABLE 5

Wear of Dry Samples (FlakeTest)

| Comparative Formula Y mascara Treated lashes | Inventive Formula X |
|---|---|
| 5-High Number of Grains | 2-Few Grains |

Figure 3:
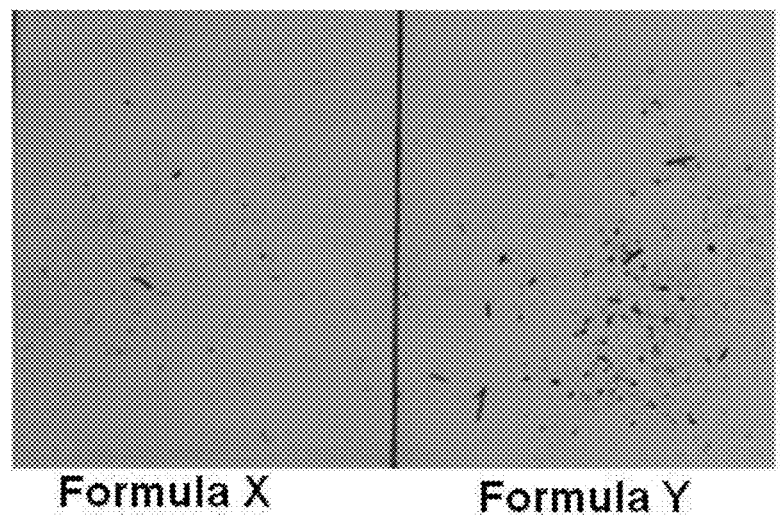
FIG. 3 is an image of blotting paper showing the results of a flake test comparison between a commercially available mascara (Formula Y) and a mascara according to the invention (Formula X). This figure shows that the mascara of the invention is less likely to dry and flake or than the commercially available mascara comparator.

As shown in Table 5 and FIG. 3, the compositions of the invention containing a sucrose fatty acid ester are less prone to flake off the lashes than the comparator mascara, which does not include a sucrose fatty acid ester.

Ease of Removal Test:

1.5 mL of makeup remover was applied on a piece of cotton pad (common method of removal). Each sample was held tightly between the pieces of cotton folds for 10 seconds, then withdrawn gently. The soaked cotton was changed and the process was repeated with fresh cotton pads each time until all makeup was removed from the sample (if possible). Results are expressed in number of cotton pads used for the majority of makeup removal in relation to the total number of cotton pads used to remove the makeup. The results are shown in Table 6 below.

TABLE 6

Ease of RemovalTest Results

| Sample | # of Cotton Pads for Full Removal | # of Cotton Pads for Majority of Removal |
|---|---|---|
| Comparator Commercial Mascara-Formula Y | 13 | 10 |
| Mascara of Invention-Formula X | 9 | 7 |

Figure 4A:
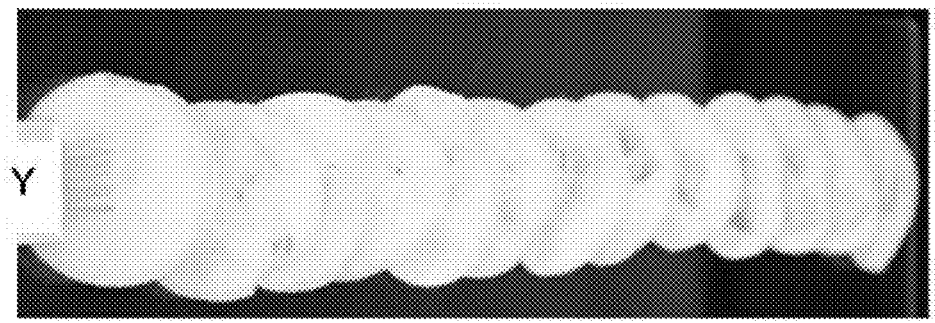
FIG. 4A and FIG. 4B are images of blotting paper showing the results of an ease of removal test comparing a commercially available mascara and a mascara according to the invention. This figure shows that the mascara of the invention (Formula X, FIG. 4B) is more easily removed from the lashes as it requires fewer pads to remove than the commercially available mascara comparator (Formula Y, FIG. 4A).
Figure 4B:
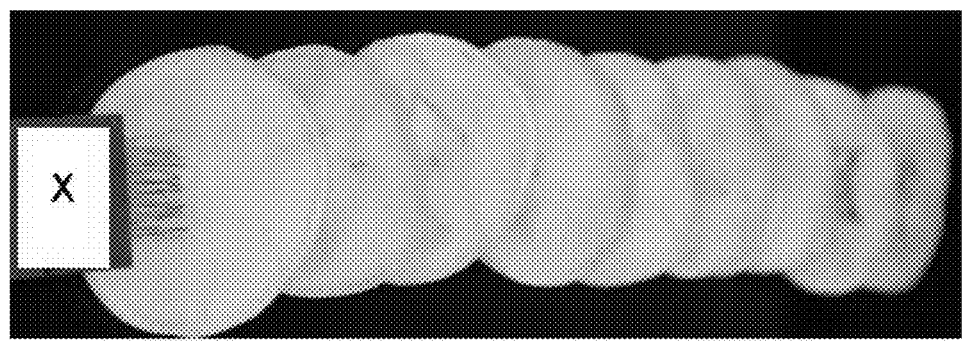

As shown in Table 6 above and FIG. 4 below, the composition of the invention containing a sucrose fatty acid ester (FIG. 4B) was more easily removed from test lashes with the makeup remover (it takes fewer pads to remove the mascara) than the commercially-available comparator mascara (FIG. 4A), which does not include a sucrose fatty acid ester.

Homogeneous, Uniform Coverage Test:

Mascara was applied onto each set of fake lashes as follows:

The mascara wand was dipped into the test mascara composition once and twisted; excess product was removed from the tip of the wand.

The blink simulator was run for eight (8) rotations with each lash set.

The mascara wand was dipped into the mascara composition once again and twisted; excess product was removed from the tip of the brush.

The blink simulator was run for seven (7) rotations for each lash set.

Each lash set was allowed to air-dry in the laboratory for thirty (30) minutes.

6 lash sets were prepared and evaluated for each formula. Images were taken of each lash set.

Figures 5A, 5B:
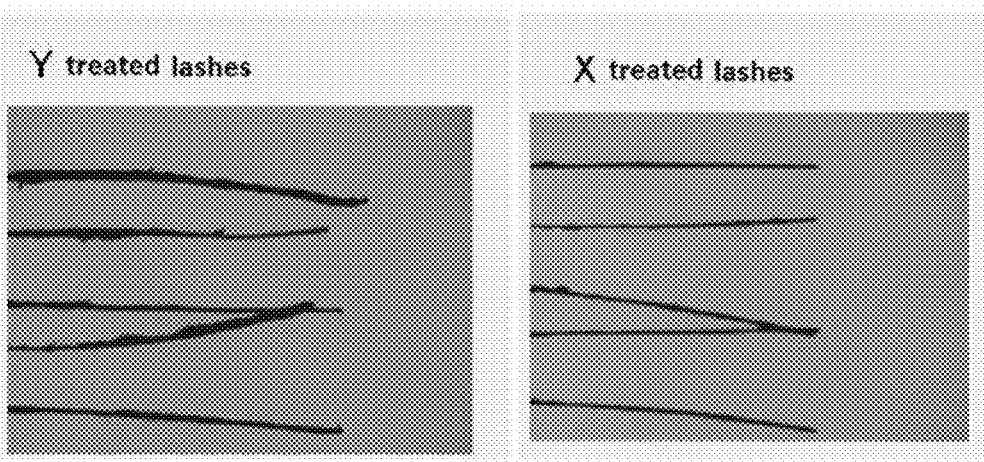
FIG. 5A and FIG. 5B are images showing the results of a test for assessing uniform coverage of test mascara compositions. As shown in these figures, in the lashes treated with the mascara of the composition Formula X (FIG. 5B), the mascara film is deposited more evenly (smoother and more consistent) than in the lashes treated with the commercially available mascara of Formula Y (FIG. 5A).

The results of this test are shown below in FIGS. 5A and 5B. As shown in these figures, in the lashes treated with the mascara Formula X (FIG. 5B), the mascara film is deposited more evenly (smoother and more consistent) than in the lashes treated with the commercially-available mascara Formula Y (FIG. 5A).

Tests for Buildability, Playtime and Fewer Clumps:

In this test, a mascara composition of the invention (Formula X) was compared with two commercially available mascara compositions: Formula Y and Covergirl Clump Crusher® mascara. The mascara was applied onto each lash set following the same procedure as described above for the Homogeneous/Uniform Coverage Test. Six (6) lash sets were prepared and evaluated for each of the three mascara compositions tested. Images were taken of each lash set. The number of clumps was evaluated by visual inspection. The results of this test are shown in Table 7 below.

TABLE 7

Average Clumps After Application

| Mascara Formula X | Mascara Formula Y | Clump Crusher |
|---|---|---|
| 6 | 12 | 9.8 |

Figure 6A:
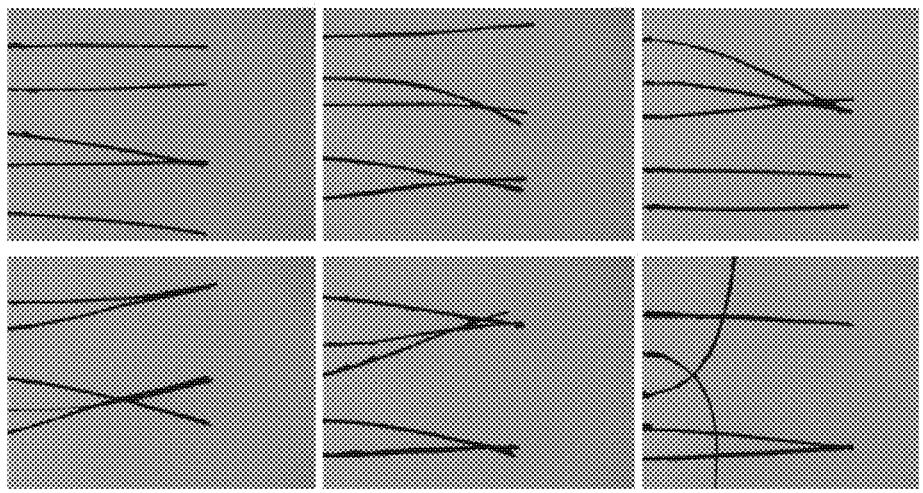
FIG. 6A, FIG. 6B and FIG. 6C are images showing the results of a test for assessing clumping of mascaras. As shown in these figures, lashes treated with the mascara of the invention Formula X (FIG. 6A) are smoother and have fewer clumps than those treated with either of two commercially available comparator mascaras; Formula Y (FIG. 6B) or Covergirl Clump Crusher® mascara (FIG. 6C).
Figure 6B:
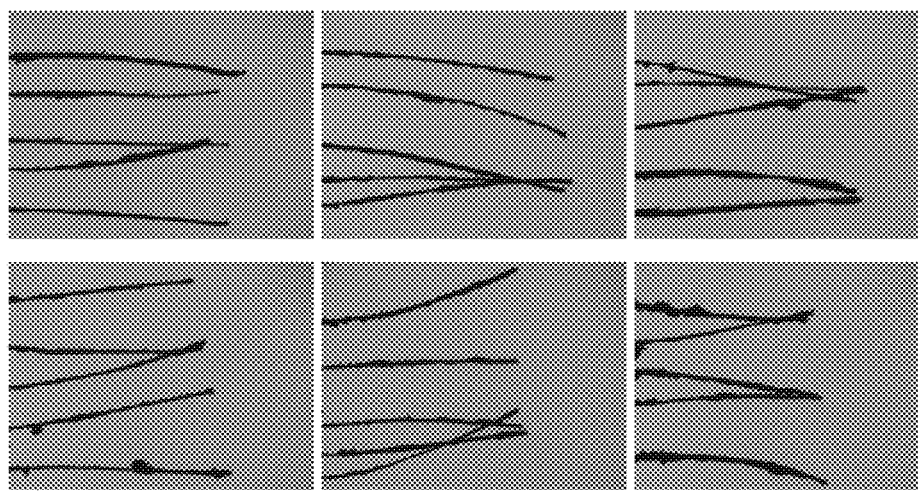
Figure 6C:
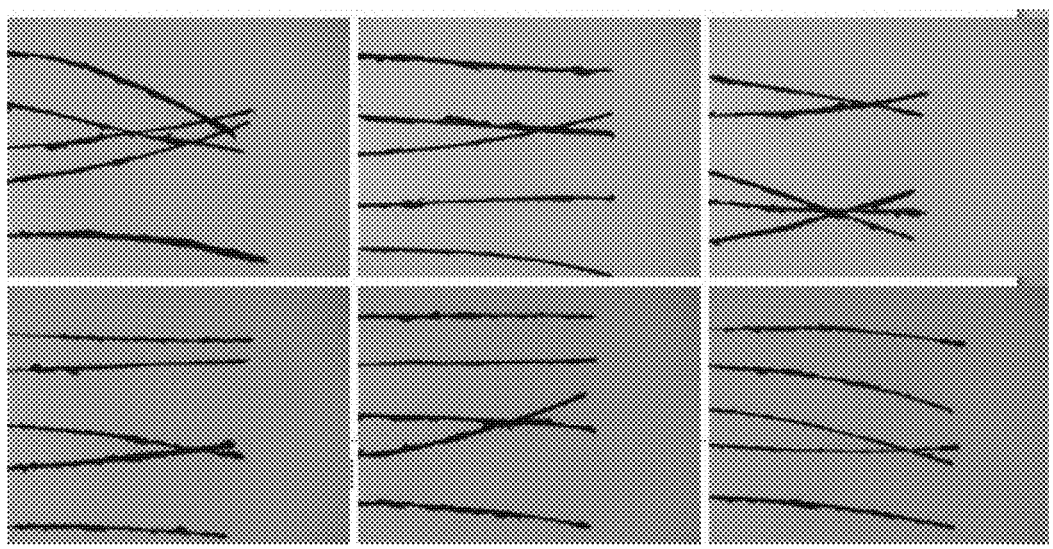

As is shown if Table 7 above and FIG. 6 below, lashes treated with the mascara of the invention, Formula X (FIG. 6A), are smoother and have fewer clumps than those treated with either of the commercially available comparator mascaras; Formula Y (FIG. 6B) or Covergirl Clump Crusher mascara (FIG. 6C).

Test for Color Intensity: Wet Masstone LAB Evaluation

Two sets of lashes were independently treated with either the inventive mascara Formula X or commercially-available comparator mascara Formula Y. The color intensity of the lashes was then measured using a colorimetric spectrophotometer.

The colorimetric spectrophotometer measures the entire visible spectrum of light (rainbow) being reflected from a sample and then using mathematical tables representing the human eye color sensitivity and mathematical tables representing the color output of different light sources, calculates the result.

Color Scales:

The color scales used for this test are the Hunter L,a,b and the CIE L*,a*,b* scales. These are 3-dimensional scales. Both are based on the opponent-colors theory that states that the red, green and blue human eye cone responses are re-mixed into black-white, red-green, and yellow-blue, opponent coders as they move up the optic nerve to the brain.

The L,a,b type of scales simulate this as:
L (lightness) axis—0 is black, 100 is white
a (red-green) axis—positive values are red; negative values are green and 0 is neutral
b (yellow-blue) axis—positive values are yellow; negative values are blue and 0 is neutral All colors that can visually be perceived can be measured in L,a,b scale. This test specifically refers to the L values as it is the measure of black versus white. As 0 is black, the lower the L value, the darker the color. The results of this test are provided below in Table 8.

TABLE 8

Wet Masstone LAB Evaluation Results

| Results: wet masstone evaluation | L* |
| --- | --- |
| Comparator Formula Y | 32.84 |
| Inventive Formula X | 28.44 |

What is claimed is:

1. A mascara composition comprising:
    (a) from about 0.1% to about 30% of at least one liquid fatty substance;
    (b) from about 3.3% to about 20% of an emulsifying system comprising (i) from about 0.3% to about 5% of at least one sucrose fatty acid ester; and (ii) from about 1% to about 10% of at least one polysorbate co-emulsifier;
    (c) from about 0.2% to about 10% of at least one viscosity increasing agent;
    (d) from about 5% to about 40% of at least one film forming system comprising (i) from about 1% to about 20% of at least one film forming polymer selected from styrene/acrylates/ammonium methacrylate copolymers, and (ii) from about 0.2% to about 5% of at least one co-film former; and
    (e) from about 30% to about 70% of water;
wherein ratio of the sucrose fatty acid ester to the co-emulsifier is between about 1:1 to about 1:20, by weight based on the total weight of the composition as a whole, said composition having a viscosity from about 4.7 Pa*s to about 16.5 Pa*s and a pH of 6.5-8.5.

2. A mascara composition comprising:
    (a) from about 0.1% to about 30% of at least one liquid fatty substance;
    (b) from about 3.3% to about 20% of an emulsifying system comprising (i) from about 0.3% to about 5% of at least one sucrose fatty acid ester; and (ii) from about 1% to about 10% of at least one polysorbate co-emulsifier;
    (c) from about 0.20% to about 10% of at least one viscosity increasing agent;
    (d) from about 5% to about 40% of at least one film forming system comprising (i) from about 1% to about 20% of at least one film forming polymer selected from styrene/acrylates/ammonium methacrylate copolymers, and (ii) from about 0.2% to about 5% of at least one co-film former;
    (e) from about 30% to about 70% of water; and
    (f) from about 1% to about 40% of at least one pigment;
wherein ratio of the sucrose fatty acid ester to the co-emulsifier is between about 1:1 to about 1:20, by weight based on the total weight of the composition as a whole, said composition having a viscosity from about 4.7 Pa*s to about 16.5 Pa*s and a pH of 6.5-8.5.

3. An oil-in-water emulsion comprising:
    (1) an oily phase comprising:
        (a) from about 0.1% to about 30% of at least one liquid fatty substance; and
        (b) from about 3.3% to about 20% of an emulsifying system comprising (i) from about 0.3% to about 5% of at least one sucrose fatty acid ester; and (ii) from about 1% to about 10% of at least one polysorbate co-emulsifier; and
    (2) an aqueous phase comprising:
        (c) from about 0.20% to about 10% of at least one viscosity increasing agent;
        (d) from about 5% to about 40% of at least one film forming system comprising (i) from about 1% to about 20% of at least one film forming polymer selected from styrene/acrylates/ammonium methacrylate copolymers, and (ii) from about 0.2% to about 5% of at least one co-film former;
        (e) from about 30% to about 70% of water; and
        (f) from about 1% to about 40% of at least one pigment;
wherein the oily phase is dispersed in the aqueous phase, said emulsion having a viscosity from about 4.7 Pa*s to about 16.5 Pa*s and a pH of 6.5-8.5, the ratio of the sucrose fatty acid ester to the co-emulsifier is between about 1:1 to about 1:20, and the ratio of the emulsifying system to the final emulsion is between about 1:6 to about 1:30, by weight, all weights being relative to the total weight of the emulsion.

4. The mascara composition of claim 2, wherein the liquid fatty substance is selected from the group comprising cetyl PEG/PPG-10/1 dimethicone, dimethicone, hydrogenated polyisobutene, PEG-12 dimethicone, dimethiconol and mixtures thereof.

5. The mascara composition of claim 4, wherein the sucrose fatty acid ester is selected from sucrose cocoate, sucrose laurate, sucrose myristate, sucrose palmitate, sucrose polystearate, sucrose tristearate, sucrose distearate, sucrose stearate, sucrose dilaurate, sucrose hexaerucate, sucrose oleate, sucrose pentaerucate, sucrose polybehenate, sucrose polycottonseedate, sucrose polylaurate, sucrose polylinoleate, sucrose polypalmate, sucrose polyoleate, sucrose polysoyate, sucrose ricinoleate, sucrose tetraisostearate, sucrose tribehenate, sucrose hexaoleate/hexapalmitate/hexastearate, sucrose hexapalmitate, sucrose trilaurate, and mixtures thereof.

6. The mascara composition of claim 5, wherein the sucrose fatty acid ester is selected from sucrose laurate, sucrose myristate, sucrose palmitate, sucrose polystearate, sucrose tristearate, sucrose distearate, sucrose stearate, and mixtures thereof.

7. The mascara composition of claim 5, wherein the viscosity increasing agent is selected from ammonium polyacryloyldimethyl taurate, ammonium acryloydimethyltaurate/steraeth-25 methacrylate crosspolymer, sorbitol/sebacic acid copolymer behenate, ethylenediamines/stearyl dimer dilinoleate copolymer, and mixtures thereof.

8. The mascara composition of claim 7, wherein the film forming polymer is selected from
olefin/acrylate grafted polymer;
styrene/acrylates/ammonium methacrylate copolymer;
acrylates/ethylhexyl acrylate/hema copolymer; acrylates/diethylaminoethyl methacrylate/ethylhexyl acrylate copolymer;
and mixtures thereof.

9. The mascara composition of claim 8, wherein the co-film former is a polymer selected from divinyldimethicone/dimethicone copolymer, vinylpyrrolidone/Eicosene copolymer, and mixtures thereof.

10. The mascara composition of claim 9, wherein the liquid fatty substance is present in the composition in an amount of from about 3% to about 15%, by weight relative to the total weight of the composition.

11. The mascara composition of claim 10, wherein the liquid fatty substance is present in the composition in an amount of about 4% to about 13%, by weight relative to the total weight of the composition.

12. The mascara composition of claim 10, wherein the sucrose fatty acid ester is present in the composition in an amount of from about 1% to about 4% by weight relative to the total weight of the composition.

13. The mascara composition of claim 12, wherein the co-emulsifier is present in the composition in an amount from about 2% to about 7%, by weight relative to the total weight of the composition.

14. The mascara composition of claim 13, wherein the viscosity increasing agent is present in the composition in an amount from about 0.5% to about 6%, by weight relative to the total weight of the composition.

15. The mascara composition of claim 14, wherein the film former is present in the composition in an amount from about 3% to about 12%, by weight relative to the total weight of the composition.

16. The mascara composition of claim 15, wherein the co-film former is present in the composition in an amount from about 1% to about 3%, by weight relative to the total weight of the composition.

17. The mascara composition of claim 2, further comprising one or more ingredients selected from tributyl citrate, texanol ester alcohol, diisobutyl adipate, an ester of tertbutyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, butylene glycol, caprylyl glycol, propylene glycol n-butyl ether, dipropylene glycol dibenzoate, dipropylene glycol dimethyl ether, propylene glycol methyl ether acetate, propylene glycol propyl ether, PEG-12 dimethicone, methyl lactate, ethyl lactate, isopropyl lactate, amino methyl propanediol, t-butyl alcohol, silica, potassium sorbate, sodium dehydroacetate, pentaerythrityl tetra-di-t-butyl hydroxyhydrocinnamate, sodium acrylate/sodium acryloydimethyl taurate copolymer, sodium acrylate/sodium acryloydimethyl taurate copolymer, sorbitan oleate, and mixtures thereof.

18. The mascara composition of claim 10, wherein the water is present in an amount of from about 40% to about 60%, by weight relative to the total weight of the composition.

19. The mascara composition of claim 10, further comprising a solvent selected from butylene glycol, caprylyl glycol, aminomethyl propanediol, phenoxyethanol, and mixtures thereof.

20. The mascara composition of claim 10, wherein the pigment is selected from titanium dioxide, zirconium oxide, zinc oxide, cerium oxide, iron oxides, chromium oxide, manganese violet, ultramarine blue, chromium hydrate, ferric blue, carbon black, titanium mica with iron oxides, titanium mica with ferric blue or chromium oxide, and mixtures thereof.

21. The mascara composition of claim 2, wherein the mascara composition is wax free.

22. A method of improving at least one property chosen from long wear, comfort, playtime, buildability, color intensity, ease of removal, water and/or oil-resistance, shine, adhesion, malleability, and transfer resistance and ease of removal properties in a cosmetic composition comprising including in the cosmetic composition:
(a) from about 0.1% to about 30% of at least one liquid fatty substance;
(b) from about 3.3% to about 20% of an emulsifying system comprising (i) from about 0.3% to about 5% of at least one sucrose fatty acid ester; and (ii) from about 10% to about 10% of at least one co-emulsifier;
(c) from about 0.20% to about 10% of at least one viscosity increasing agent; and
(d) from about 5% to about 40% of at least one film forming system comprising (i) from about 1% to about 20% of at least one film forming polymer selected from a styrene/acrylates/ammonium methacrylate copolymer, and (ii) from about 0.2% to about 5% of a co-film former;
wherein ratio of the sucrose fatty acid ester to the co-emulsifier is between about 1:1 to about 1:20, by weight based on the total weight of the composition as a whole, said composition having a viscosity from about 4.7 to about 16.5 Pa*s and a pH of 6.5-8.5.

23. A method of making up or enhancing the appearance of eyelashes by applying to the lashes topically a composition comprising:
(a) from about 0.1% to about 30% of at least one liquid fatty substance;
(b) from about 3.3% to about 20% of an emulsifying system comprising (i) from about 0.3% to about 5% of at least one sucrose fatty acid ester; and (ii) from about 1% to about 10% of at least one co-emulsifier;
(c) from about 0.20% to about 10% of at least one viscosity increasing agent;
(d) from about 5% to about 40% of at least one film forming system comprising (i) from about 1% to about 20% of at least one film forming polymer selected from a styrene/acrylates/ammonium methacrylate copolymer, and (ii) from about 0.2% to about 5% of at least one co-film former;
(e) from about 30% to about 70% water; and
(f) from about 1% to about 40% of at least one pigment;
wherein ratio of the sucrose fatty acid ester to the co-emulsifier is between about 1:1 to about 1:20, by weight based on the total weight of the composition as a whole, said composition having a viscosity from about 4.7 to about 16.5 Pa*s and a pH of 6.5-8.5.

24. The mascara composition of claim 1, wherein the mascara composition comprises 5% or less of wax.

25. The mascara composition of claim 2, wherein the mascara composition comprises 5% or less of wax.

26. The oil-in-water emulsion of claim 3, wherein the emulsion comprises 5% or less of wax.

\* \* \* \* \*